(12) United States Patent
Dhaon et al.

(10) Patent No.: US 7,700,614 B2
(45) Date of Patent: Apr. 20, 2010

(54) ONE POT SYNTHESIS OF TETRAZOLE DERIVATIVES OF RAPAMYCIN

(75) Inventors: Madhup K. Dhaon, Mundelein, IL (US); Chi-nung Hsiao, Taipei County (TW); Subhash R. Patel, Chicago, IL (US); Peter J. Bonk, Westerly, RI (US); Sanjay R. Chemburkar, Gurnee, IL (US); Yong Chen, Lake Villa, IL (US)

(73) Assignee: Abbott Laboratories, Abbott Park, IL (US)

( * ) Notice: Subject to any disclaimer, the term of this patent is extended or adjusted under 35 U.S.C. 154(b) by 561 days.

(21) Appl. No.: 11/300,671

(22) Filed: Dec. 14, 2005

(65) Prior Publication Data

US 2008/0167335 A1 Jul. 10, 2008

(51) Int. Cl.
*C07D 498/18* (2006.01)
(52) U.S. Cl. .................. 514/291; 540/456
(58) Field of Classification Search ............. 540/456; 514/291
See application file for complete search history.

(56) References Cited

U.S. PATENT DOCUMENTS 6,015,815 A 1/2000 Mollison

OTHER PUBLICATIONS

International Search Report for PCT/US06/61909, filed Dec. 12, 2006, mailed Oct. 1, 2007, 7 pgs.

*Primary Examiner*—Bruck Kifle
(74) *Attorney, Agent, or Firm*—Squire, Sanders & Dempsey L.L.P.

(57) ABSTRACT

A single-step, one-pot process to obtain zotarolimus and other rapamycin derivatives on large scale is presented, which improves currently available synthesis schemes. In one embodiment, dried rapamycin is dissolved in isopropylacetate (IPAc). The solution is cooled, and 2,6-Lutidine is added, followed slowly adding triflic anhydride at −30° C. Salts are then removed by filtration. Tetrazole, followed by a tert-base diisopropylethylamine (DIEA) is added to the triflate solution. After incubation at room temperature, the product is concentrated and purified by a silica gel column using THF/heptane as eluant. The fractions containing the product are collected, concentrated, and purified again using an acetone/heptane column. The product containing fractions are concentrated. The product is dissolved in t-BME and precipitated with heptane. The solids are dissolved in acetone, treated with butylated-hydroxy toluene (BHT), and the solution concentrated. The process is repeated twice with acetone to remove solvents. At least one stabilizing agent is added, such as BHT at 0.5% before drying.

37 Claims, 2 Drawing Sheets

ONE POT SYNTHESIS OF TETRAZOLE DERIVATIVES OF RAPAMYCIN

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable.

TECHNICAL FIELD

The present invention relates to novel methods of synthesizing analogs of rapamycin. The analogs are useful in antiproliferative and immuno-modulatory applications.

BACKGROUND OF THE INVENTION

Introduction

Sirolimus

As the moai gazed down, a Canadian expedition in 1964 dug in the dirt to unearth a fungus that produced a powerful immunosuppressing, anti-fungal and anti-cell proliferation molecule. From Easter Island to laboratories in Canada, the fungus landed in Suren Sehgal's hands, who elucidated the properties of a purified compound of the fungus *Streptomyces hygroscopicus* in 1972, but this finding was abandoned, a victim of corporate priorities. Sehgal resurrected research in 1987 and developed the compound as an immunosuppressant. Today, rapamycin (christened after Rapa Nui, the name by which the Easter Island natives knew their homeland) is used to reduce the risk of organ transplants and the side effects of stents, and is being investigated as an anti-tumor pharmaceutical.

Rapamycin, also known as sirolimus, is a macrocyclic triene antibiotic that inhibits fungal growth, particularly against *Candida albicans*, both in vitro and in vivo (Baker et al., 1978; Sehgal, 1975; Sehgal, 1976; Sehgal et al., 1975; Vezina et al., 1975). Sirolimus alone (Surendra, 1989) or in combination with picibanil (Eng, 1983) has been shown to have anti-tumor activity. In 1977, sirolimus was shown to be effective as an immunosuppressant in experimental models for allergic encephalomyelitis (a model for multiple sclerosis), adjuvant arthritis, and rheumatoid arthritis (Martel et al., 1977). Sirolimus also effectively inhibits the formation of IgE-like antibodies (Martel et al., 1977). Its structure is depicted below (VI).

ABT-578 [40-epi-(1-tetrazolyl)-rapamycin], known better today as zotarolimus, is a semi-synthetic macrolide triene antibiotic derived from sirolimus. Zotarolimus is a potent inhibitor of T-cell lymphocyte proliferation, similar to its precursor zotarolimus. Zotarolimus has found exceptional applications in coating cardiovascular stents, especially drug-eluting stents (DES's) to minimize restenosis (Mollison et al., 2003). Zotarolimus exists in two isomeric forms, a major pyran (6-member isomer at 10 position; 1) and a minor oxepane isomer (7 member isomer at 9 position; 2), both of which are N-1 isomers (Mollison, 2000).

Other chemical modifications of rapamycin have been attempted. These include the preparation of mono- and di-ester derivatives of rapamycin (Caufield, 1992), 27-oximes of rapamycin (Failli, 1992a); 40-oxo analog of rapamycin (Caufield, 1991); bicyclic rapamycins (Kao, 1992a); rapamycin dimers (Kao, 1992b); silyl ethers of rapamycin (Failli, 1992b); and arylsulfonates and sulfamates (Failli, 1993).

In addition to its anti-fungal, immunosuppressant and anti-tumor activities, sirolimus reduces neointimal proliferation in animal models, as well as the rate of restenosis in humans. Sirolimus also exhibits an anti-inflammatory effect, a characteristic which supported its selection as an agent for the treatment of rheumatoid arthritis. Stents coated with analogues of sirolimus, such as everolimus and especially zotarolimus, are effective at preventing restenosis in clinical trials.

Stents and Other Implantable Medical Devices

Stents are used to treat serious decreases in vessel or duct diameter due to a variety of diseases and conditions, especially atherosclerotic diseases, and are often used after angioplasty. While frequently used in arteries, stents are also used in other structures, including veins, bile ducts, esophagus, trachea, large bronchi, ureters, and urethras. Stents are the innovation of the English dentist Charles Stent (1845-1901).

While effective in treating deleterious lumen narrowing, vascular stents in an instance of medical irony, also risk re-creating the condition that they were used to treat. Stents can incur the development of thick endothelial tissue inside the lumen—the neointima. While the degree of development varies, the neointima can grow to occlude the vessel lumen, a type of restenosis.

(VI)

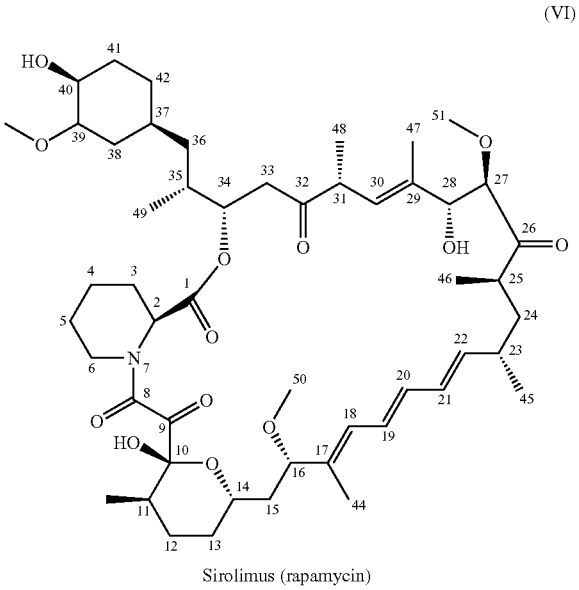

Sirolimus (rapamycin)

SCHEME 1
The isomers of ABT-578 (zotarolimus)

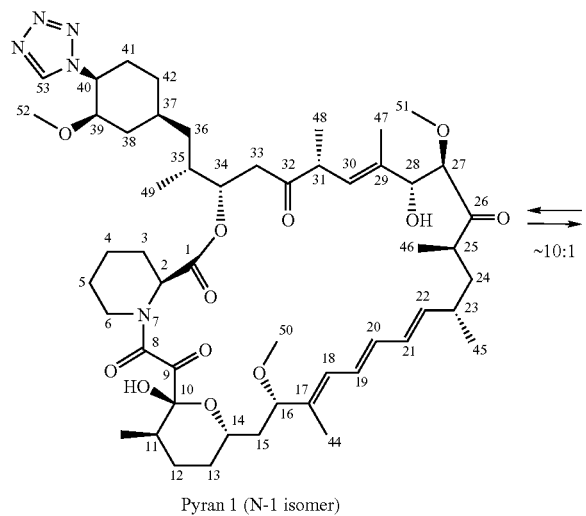

Pyran 1 (N-1 isomer)

(Ia)

~10:1

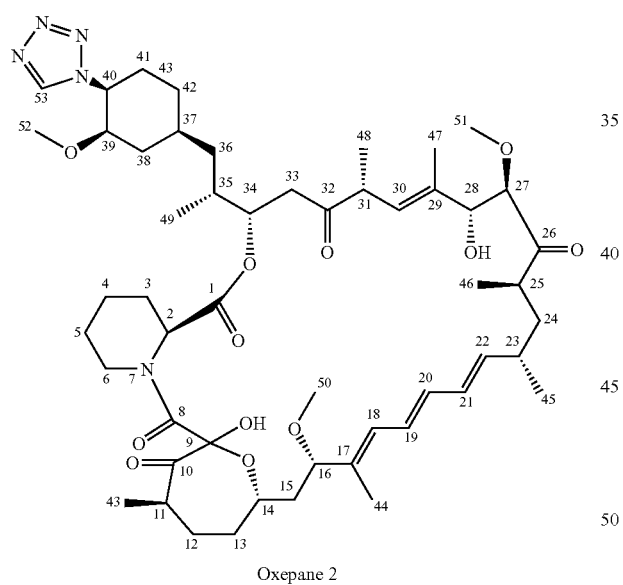

Oxepane 2

(Ib)

Previous Syntheses of Zotarolimus

Mollison presented several methods to generate zotarolimus from sirolimus (Mollison, 2000). For example, C-40 hydroxyl of sirolimus is activated with the formation of triflate, and the triflate is then purified by column chromatography. During triflate purification, some of the activated intermediate reverts to sirolimus and its epimer, epi-sirolimus, due to presence of the water during chromatography. The purified triflate is then reacted in a second step with tetrazole to produce the 40-epi-tetrazole derivative of sirolimus, that is, zotarolimus. The crude product is then purified by column chromatography. However, even with this purification, the end product could contain sirolimus and epi-sirolimus impurities.

SUMMARY OF THE INVENTION

Figure 1:
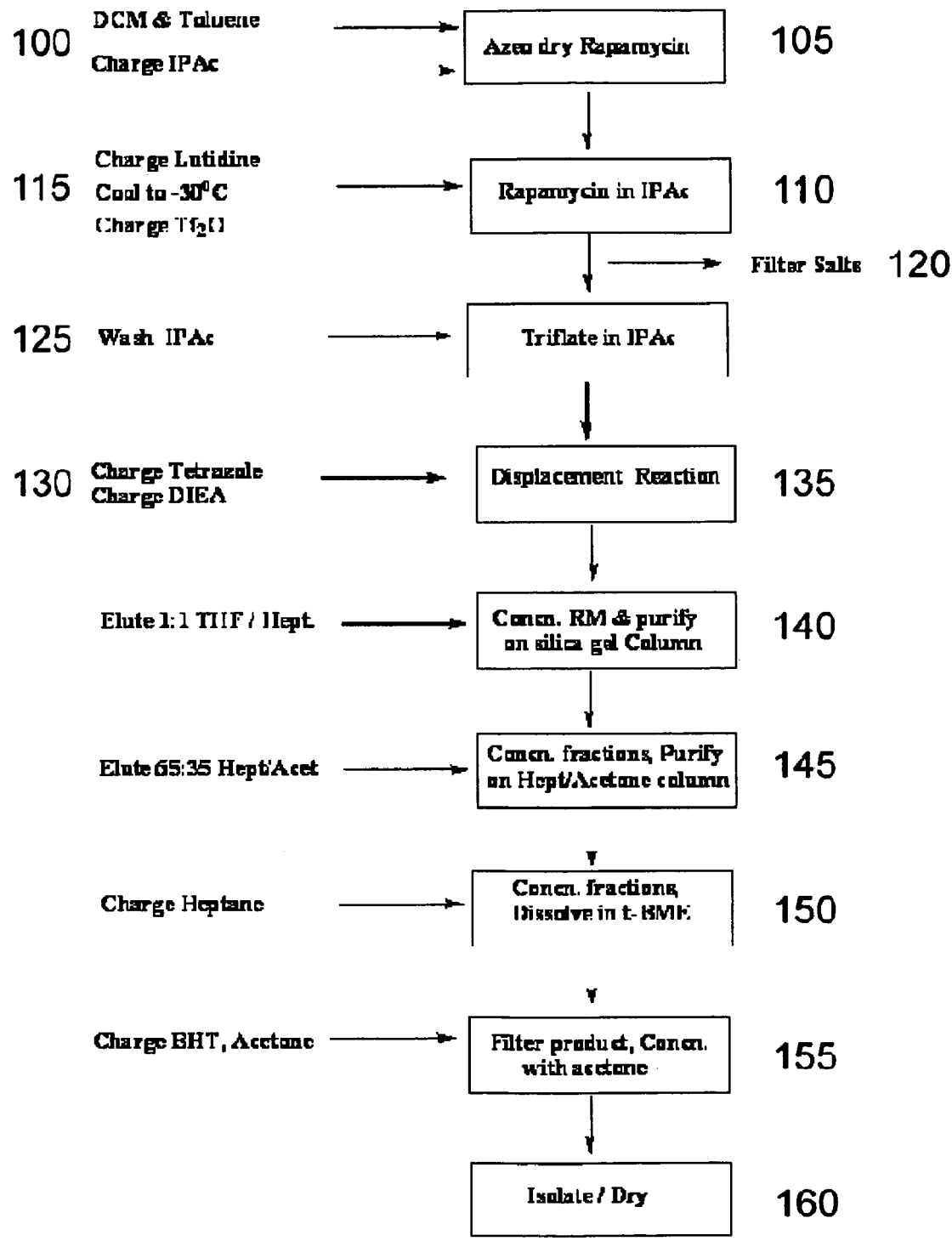
FIG. 1 shows a flow diagram of an embodiment of a one-pot method of making zotarolimus according to the present invention.

The invention provides methods of performing in a single pot derivatives of rapamycin, and provides for compositions made by such methods that include anti-oxidants.

In a first aspect, the invention provides methods for preparing a molecule of formula I:

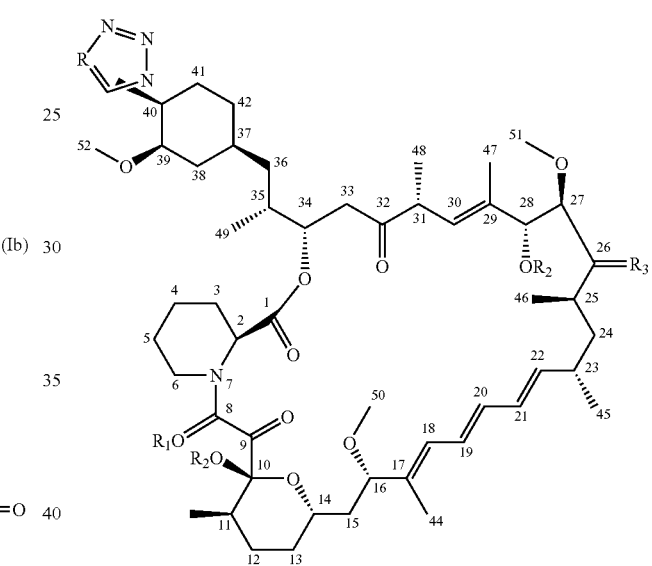

Where a molecule in a first step (a) of formula II:

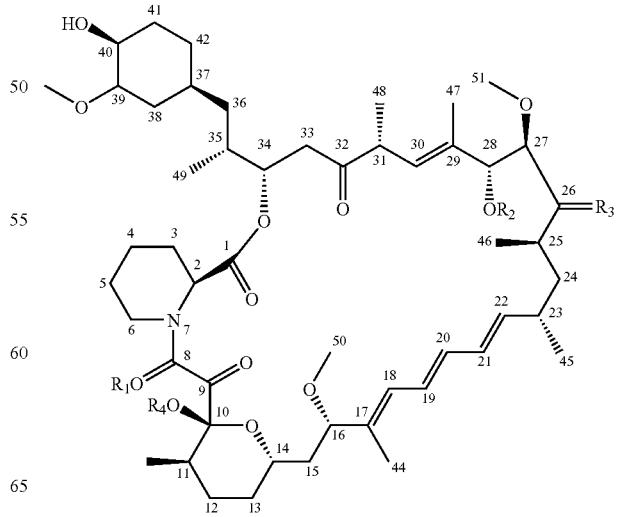

is reacted with triflic anhydride to produce a molecule of formula III:

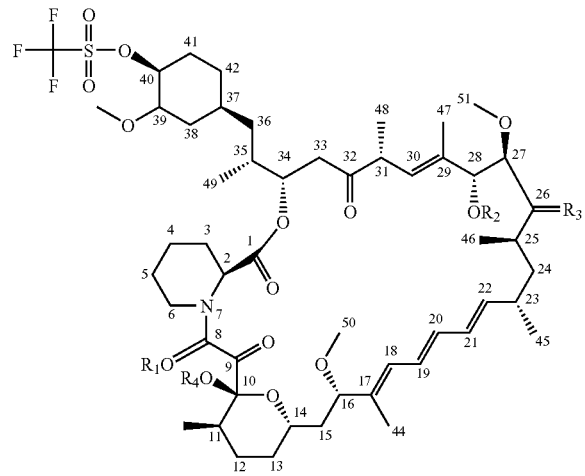

and then reacting the molecule of formula III in a second step (b) with a molecule of formula IV:

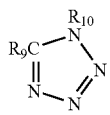

wherein $R_1$ is selected from the group consisting of =O (H, H), and (H, OH);

$R_2$ and $R_5$ are independently selected from the group consisting of H, —C(=O)$R_6$, —C(=O)O$R_6$, —C(=O)NH$R_6$, and —C(=S)O$R_6$;

$R_3$ is selected from the group consisting of =O and O$R_5$; or $R_2$ and $R_3$ can be taken together to form moiety of formula A—C($R_7$)($R_8$)—O—B, where A is a bond to oxygen bonded to carbon 28 and B is a bonded to carbon 28 as defined above;

$R_4$ is selected from the group consisting of H and $C_1$-$C_4$ alkyl;

$R_6$ is selected from the group consisting of $C_1$-$C_{10}$ alkyl, $C_3$-$C_6$ cycloalkyl, aryl groups, and heterocyclic groups;

$R_7$ and $R_8$ are independently selected from the group consisting of H, $C_1$-$C_6$ alkyl, or $R_7$ and $R_8$ taken together are =O $R_9$ and $R_{10}$ are independently selected from the group consisting of H, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof.

Step (a) of the method is carried out in the presence of a non-nucleophilic base, such as 2,6-dimethylpyridine or diisopropylethyl amine. Step (a) is also carried out in a solvent, such as isopropyl acetate or dichloromethane. In some embodiments, dichloromethane is exchanged to isopropyl acetate before or during step (b).

In the molecule represented by formula IV, $R_{10}$ can be H, and $R_9$ is H, methyl, or phenyl. In some embodiments, $R_9$ and $R_{10}$ are H.

Step (b) is also carried out in the presence of a solvent, such as an aprotic solvent; the aprotic solvent can be, for example, perfluorohexane, α,α,α-trifluorotoluene, pentane, hexane, cyclohexane, methylcyclohexane, decahydronaphthalene, carbon tetrachloride, dioxane, fluorotrichloromethane, benzene, toluene, triethyl amine, carbon disulfide, diisopropyl ether, diethyl ether, t-butyl methyl ether, chloroform, ethyl acetate, 1,2-dimethoxyethane, 2-methoxyethyl ether, tetrahydrofuran, 1,2-dimethoxyethane, tetrahydrofuran, methylene chloride, pyridine, 2-butanone, acetone, hexamethylphosphoramide, N-methylpyrrolidinone, nitromethane, dimethyl formamide, acetonitrile, sulfolane, dimethyl sulfoxide, diisopropyl ethyl amine, isopropyl acetate, dichloromethane, dimethylamine, N,N-dimethylformamide or propylene carbonate. In some embodiments, step (b) is carried out in the presence of diisopropyl ethyl amine and either isopropyl acetate, dichloromethane, 1,2-dimethoxyethane, tetrahydrofuran, acetonitrile, dimethylamine, or N,N-dimethylformamide. In other embodiments, step (b) is carried out in diisopropyl ethyl amine and either isopropyl acetate or dichloromethane.

In a specific embodiment, the molecule represented by formula II, $R_1$ is =O, $R_2$ is H, $R_3$ is =O and $R_4$ is H.

In another aspect, zotarolimus is provided by the novel methods of the invention from rapamycin.

In yet another aspect, the invention provides for compositions of the molecules prepared by the methods of the invention combined with anti-oxidants. Such oxidants include 3,5-di-tert-4-butylhydroxy toluene, DL-α-tocopherol, propyl gallate, ascobyl palmitate, 3-tert-butyl-4-hydroxyanisole or 2-tert-butyl-4-hydroxyanisole, and fumaric acid In one embodiment, the anti-oxidant is 3,5-di-tert-4-butylhydroxy toluene.

In another aspect, the invention provides for compositions of zotarolimus made by the methods of the invention formulated with an anti-oxidant, such as 3,5-di-tert-4-butylhydroxy toluene, DL-α-tocopherol, propyl gallate, ascobyl palmitate, 3-tert-butyl-4-hydroxyanisole or 2-tert-butyl-4-hydroxyanisole, and fumaric acid. In one embodiment, the anti-oxidant is 3,5-di-tert-4-butylhydroxy toluene.

DETAILED DESCRIPTION OF THE INVENTION

The invention provides a one-pot process for the preparation of a tetrazole analog of sirolimus at the C-40 position, producing zotarolimus, virtually eliminating the sirolimus and epi-sirolimus impurities of previous methods and presenting a more efficient method of making the pharmaceutical. In this method, triflate is generated in isopropylacetate (IPAc) or dichloromethane (DCM) as solvent in presence of a non-nucleophilic base like 2,6-Lutidine, or other substituted pyridines like 2,6-di-tert-butylpyridine or 2,4,6-collidine, pyridine, or Hunig's base diisopropylethyl amine (DIEA). When IPAc is used as a solvent during triflate formation, the salts can be filtered, and the triflate solution reacted with tetrazole in presence of DIEA. When DCM is used as a solvent during triflate formation, the solvent is switched to IPAc. Subsequently, the $S_N2$ reaction with tetrazole is carried out in IPAc and tetrazole with DIEA as a base. The crude product after removal of the solvent is purified by column chromatography in THF/heptane followed by heptane/acetone. The purified product can be isolated as a solid by treatment with t-butyl methyl ether (t-BME)/heptane. Zotarolimus thus obtained is unstable at room temperature but can be stabilized by the addition of anti-oxidants, such as BHT (2,6-di-t-butyl-4-methylphenol, butylated hydroxy toluene), 2,6-di-t-butyl-4-ethylphenol (DEP), 2,6-di-t-butyl-4-methoxyphenol (DMP).

Some of the significant advantages of the one-pot method include:

1. Eliminating purification of triflate, which, in previous methods, was a significant source of impurities in the final product;
2. Further reduction in sirolimus and epi-sirolimus byproduct levels, formed during the $S_N2$ reaction, by purifying the crude product of the method in THF:heptane;
3. Using in the $S_N2$ reaction aprotic solvents that can be easily recovered and re-used, thus reducing costs and environmental concerns incurred by previous methods;
4. Easy isolation and purification of the product by dissolving in t-BME and adding heptane or by a reverse-addition procedure;
5. Easy stabilization of the clean product by adding anti-oxidants; and
6. Easy isolation by lyophilization in acetonitrile or acetonitrile:water.

Definitions

"Pro-drug" refers to compounds which are rapidly transformed in vivo to the parent compound, for example, by hydrolysis in blood. Thorough discussions are available (Higuchi and Stella, 1987; Roche, 1987).

"Pharmaceutically acceptable pro-drugs" refers to those pro-drugs of the compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention. Particularly preferred pharmaceutically acceptable pro-drugs of this invention are pro-drug esters of the C-31 hydroxyl group of compounds of this invention.

"Pro-drug esters" refers to any of several ester-forming groups that are hydrolyzed under physiological conditions. Examples of pro-drug ester groups include acetyl, ethanoyl, pivaloyl, pivaloyloxymethyl, acetoxymethyl, phthalidyl, methoxymethyl, indanyl, and the like, as well as ester groups derived from the coupling of naturally or unnaturally-occurring amino acids to the C-31 hydroxyl group of compounds of this invention.

"Therapeutic substance" means any substance that when administered to a subject appropriately at an appropriate doses, has a beneficial effect on the subject.

When any substituent or variable (e.g., aryl, alkoxyl, $R^1$, $R^2$, $R^3$, $R^5$, $R^6$, etc.) occurs more than one time in a formula, such variable or substituent definition on each occurrence is independent of its definition at every other occurrence, unless otherwise indicated. Combinations of substituents and/or variables are in a constituent of the compounds of the invention are permissible only if such combinations result in a stable compound.

The parenthetical nomenclature used in the definition of substituents such as $R^1$ (e.g., (H, $OR^6$) is intended to reflect the substituents on both valences of the relevant atom. The invention is not limited to particular isomers and the order of moieties in the parentheses does not suggest a particular configuration.

"Acyloxy" means —OC(O)-(alkyl) and —OC(O)-(aryl).

"Alkenyl" alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl.

"Alkoxyl" means an alkyl group linked to oxygen.

"Alkyl," alone or in combination, means a straight-chain or branched-chain alkyl radical containing from 1 to about 22 carbon atoms, from about 1 to about 18 carbon atoms or from about 1 to about 12 carbon atoms. Examples of such radicals include, but are not limited to, methyl, ethyl, n-propyl, iso-propyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

"Alkylcycloalkenyl" and "alkenylcycloalkenyl" mean a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl.

"Alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl.

"Alkynyl" alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl.

"Amino" means —$NH_2$, —$N(alkyl)_2$, —NH(alkyl), —$N(aryl)_2$, and —NH(aryl).

"Aralkyl" alone or in combination, means an alkyl or cycloalkyl radical as defined above in which one hydrogen atom is replaced by an aryl radical as defined above, such as benzyl, 2-phenylethyl, and the like.

"Aryl" alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

"Cycloalkenyl" alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl.

"Cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl)hexyl, 6-(1-cyclohexen-1-1-yl) hexyl, 1-(1-cyclopenten-1-yl)nonyl and 1-(1-cyclohexen-1-yl)nonyl.

"Cycloalkyl" alone or in combination means a cycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and perhydronaphthyl.

"Cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl.

"Cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl.

"Halogen" includes fluoro-, chloro-, bromo- and iodo-.

"Heterocycle" includes a stable 5- to 7-membered mono- or bicyclic or stable 7- to 10-membered bicyclic heterocyclic ring that is either saturated or unsaturated and consists of carbon atoms and from one to three hetero-atoms independently selected from the group consisting of N, O and S, and wherein the nitrogen and sulfur hetero-atoms can be oxidized, and the nitrogen heteroatom can be quarternized, and including any bicyclic group in which a heterocyclic ring is fused to a benzene ring. The heterocyclic ring can be attached at any hetero-atom or carbon atom that results in a stable structure. Examples of heterocyclic elements include piperidyl, piperidinyl, piperazinyl, pyrimidinyl, pyridazinyl, oxazolyl, furyl, and thienyl. The heterocycle can be substituted in a manner such that carbon atoms attached to a heteroatom are not directly substituted by a heteroatom, by from one to four members that can be $C_1$-$C_6$ alkyl, aryl, hydroxyl, $C_1$-$C_6$ alkoxyl, acyloxy, amino, N-acylamino, nitro and halogen.

"Heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

"Ketone" means —C(O)—.

"N-acylamino" means —NHC(O)-(alkyl) and —NHC(O)-(aryl).

"Nitrogen-containing heterocycle" means ring structures in which 2 carbons and a nitrogen of the ring are also part of the fifteen-membered macrocyclic ligand. The ring 10 structure can contain from about 2 to about 20 or from about 4 to about 10, carbon atoms, can be substituted or unsubstituted, partially or fully unsaturated or saturated, and can also contain nitrogen, oxygen and/or sulfur atoms in the portion of the ring which is not also part of the fifteen-membered macrocyclic ligand.

"Saturated, partially saturated or unsaturated cyclic" means fused ring structures in which 2 carbons of the ring are also part of the fifteen-membered macrocyclic ligand. The ring structure can contain from about 3 to about 20 carbon atoms or from about 5 to about 10 carbon atoms, and can also contain one or more other kinds of atoms in addition to carbon. The most common of the other kinds of atoms include nitrogen, oxygen and sulfur. The ring structure can also contain more than one ring.

"Saturated, partially saturated or unsaturated ring structure" means a ring structure in which one carbon of the ring is also part of the fifteen-membered macrocyclic ligand. The ring structure can contain from about 3 to about 20 or from about 5 to about 10, carbon atoms and can also contain nitrogen, oxygen and/or sulfur atoms.

Practicing the Invention

To prepare a molecule formula I:

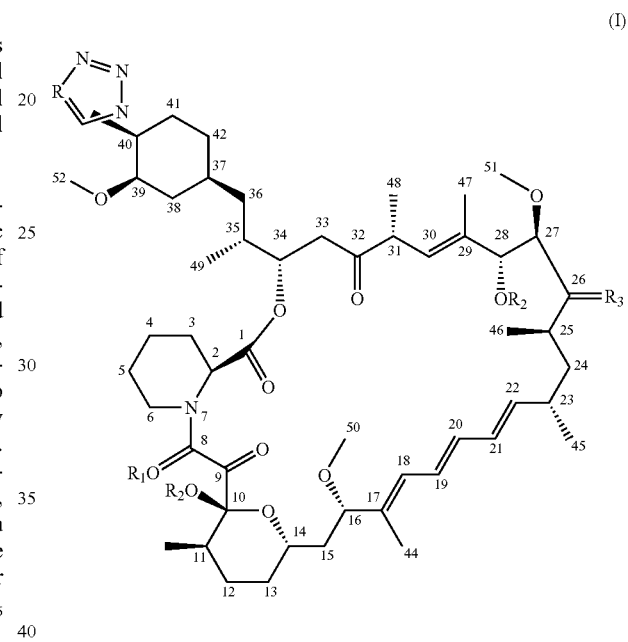

A molecule of formula II:

Wherein $R_1$ is =O (H, H), or (H, OH);

$R_2$ and $R_5$ are independently H, —C(=O)$R_6$, —C(=O)O$R_6$, —C(=O)NH$R_6$, or —C(=S)O$R_6$;

$R_3$ is =O or O$R_5$; or $R_2$ and $R_3$ can be taken together to form moiety of formula A—C($R_7$)($R_8$)—O—B, where A is a bond to oxygen bonded to carbon 28 and B is a bonded to carbon 28 as defined above;

$R_4$ is H or $C_1$-$C_4$ alkyl;

$R_6$ is $C_1$-$C_{10}$ alkyl, $C_3$-$C_6$ cycloalkyl, an aryl group, or a heterocyclic group;

$R_7$ and $R_8$ are independently H, $C_1$-$C_6$ alkyl, or $R_7$ and $R_8$ taken together are =O, is reacted with triflic anhydride to produce a molecule of formula III, completing step (a):

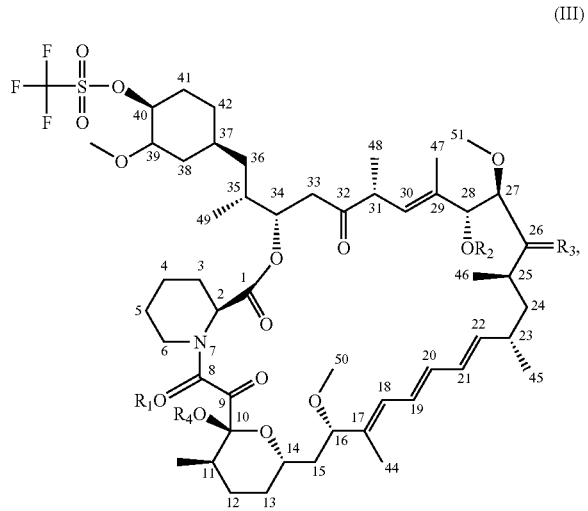

(III)

Which is then reacted with a molecule of formula IV:

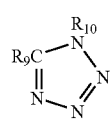

(IV)

wherein $R_9$ and $R_{10}$ are independently H, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, or combinations thereof and completing step (b).

Step (a)

In the molecule of formula II, $R_1$ is preferably O, $R_2$ is preferably H, $R_3$ is preferably O and $R_4$ is preferably H.

Base Step (a) is carried out in the presence of a non-nucleophilic base, preferably 2,6-dimethylpyridine or diisopropylethyl amine.

Solvent This step is also carried out in the presence of a solvent, such as isopropyl acetate or dichloromethane. If the solvent is dichloromethane, it can be exchanged to isopropyl acetate before or during step (b).

Step (b)

In the molecule of formula IV, $R_{10}$ is preferably H, and $R_9$ is one selected from the group consisting of H, methyl, and phenyl, and more preferably, $R_9$ and $R_{10}$ are H.

Solvent Step (b) is also carried out in the presence of a solvent, preferably an aprotic solvent. Examples of aprotic solvents include perfluorohexane, α,α,α-trifluorotoluene, pentane, hexane, cyclohexane, methylcyclohexane, decahydronaphthalene, carbon tetrachloride, dioxane, fluorotrichloromethane, benzene, toluene, triethyl amine, carbon disulfide, diisopropyl ether, diethyl ether, t-butyl methyl ether, chloroform, ethyl acetate, 1,2-dimethoxyethane, 2-methoxyethyl ether, tetrahydrofuran, 1,2-dimethoxyethane, tetrahydrofuran, methylene chloride, pyridine, 2-butanone, acetone, hexamethylphosphoramide, N-methylpyrrolidinone, nitromethane, dimethyl formamide, acetonitrile, sulfolane, dimethyl sulfoxide, diisopropyl ethyl amine, of isopropyl acetate, dichloromethane, dimethylamine, N,N-dimethylformamide and propylene carbonate. Other aprotic solvents can be used. Preferred aprotic solvents include diisopropyl ethyl amine, isopropyl acetate, dichloromethane, 1,2-dimethoxyethane, tetrahydrofuran, acetonitrile, dimethylamine, and N,N-dimethylformamide; most preferred are diisopropyl ethyl amine with either isopropyl acetate or dichloromethane.

Scheme 2 represents a summary of a preferred embodiment of the invention; FIG. 1 shows a flow diagram that outlines the steps in the one-pot process for making zotarolimus. In a first embodiment, sirolimus (commercially available or produced as described ((Paiva et al., 1991; Sehgal et al., 1975; Vezina et al., 1975) is dissolved in DCM:toluene (such as 1:2) 100. The reaction mixture is concentrated to dryness 105, and the azeo-drying process 105 is repeated 1-5 times more, more preferably 2-4 times, most preferably twice, preferably with DCM:toluene. The resulting foamy solid is dissolved in IPAc 110, and then 2,6-Lutidine is added 115. The solution is cooled to −30° C. 115. Triflic anhydride is then slowly added to the solution 115. After stirring the reaction mixture, the solution is filtered under nitrogen. The recovered salts 120 are washed with IPAc 125. To the salts is added 1-H-tetrazole and DIEA 130. The reaction mixture is stirred at room temperature (e.g., 22-25° C.) 135 and then concentrated. The crude reaction mixture is purified, using for example, a silica gel column and using, e.g., 1:1 THF:heptane to elute 140. The fractions are monitored for the N-1 isomer (which elutes more slowly than the N-2 isomer), pooled and concentrated, forming an oil. The oil is dissolved in minimum DCM and the solution loaded on a silica gel column packed in, for example, 65:35 heptane:acetone 145. The column is eluted with, for example, 65:35 heptane:acetone, the fractions monitored for the pure product, pooled and concentrated 150.

SCHEME 2
Summary of the one-pot process for synthesizing zotarolimus
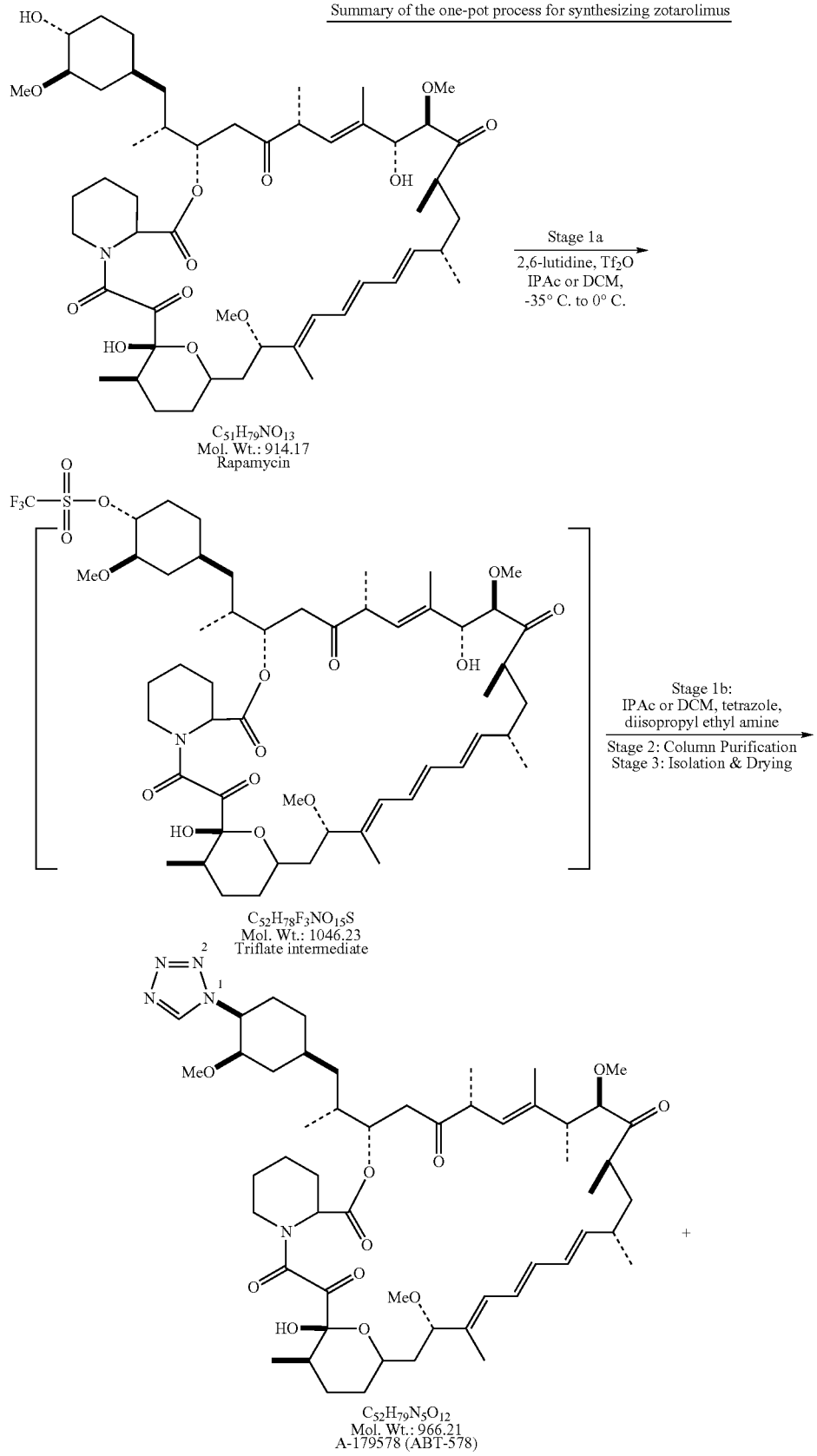

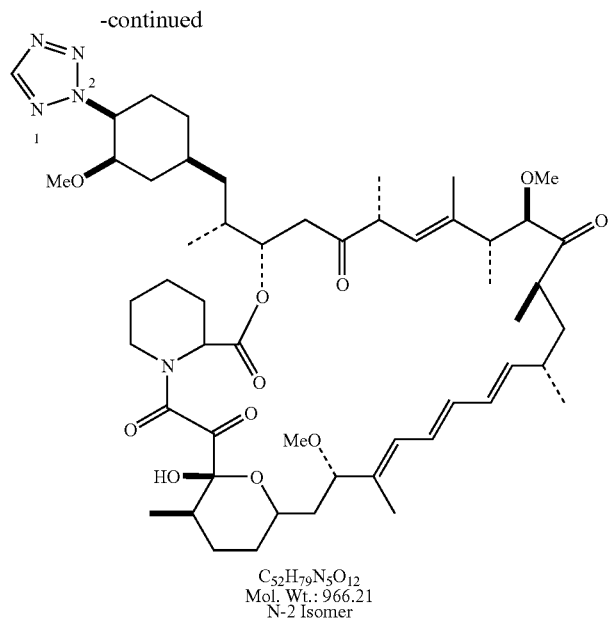

$C_{52}H_{79}N_5O_{12}$
Mol. Wt.: 966.21
N-2 Isomer

The purified product is then dissolved in t-BME, and then n-heptane is slowly added to form a precipitate while vigorously stirring the solution 150. The precipitated solids are stirred at 5-10° C., filtered, washed again with heptane, and dried on the funnel with nitrogen. The product is dissolved in acetone and treated with BHT 155. The solution is concentrated, dissolved in acetone, and then concentrated to dryness. The product is then dried under vacuum at 47° C. 160.

Figure 2:
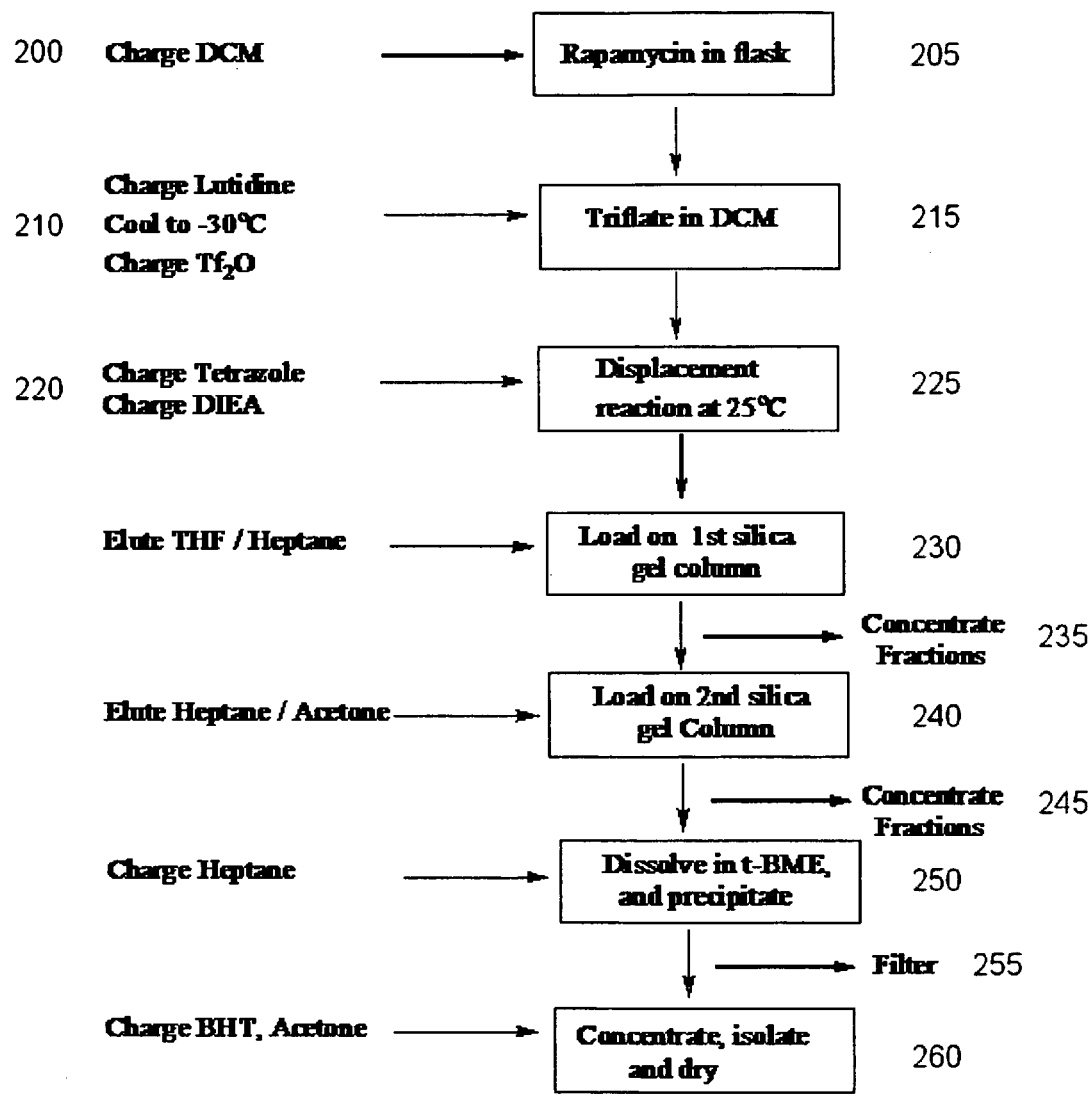
FIG. 2 shows a flow diagram of an embodiment of a one-pot method of making zotarolimus according to the present invention.

In a second preferred embodiment, a flow chart for which is shown in FIG. 2, sirolimus is dissolved in DCM 200, 205. 2,6-Lutidine is then added, the solution cooled to −30° C., and triflic anhydride slowly added 210. The reaction mixture 215 is mixed and tetrazole is added, followed by DIEA, are added 220. The reaction mixture is incubated at approximately 25° C. 225, and then loaded on silica gel columns prepared, for example, in 1:1 THF:n-heptane (v/v) 230. The crude reaction mixture is purified with 1:1 THF:n-heptane. The fractions containing the product are collected and concentrated 235. The concentrated solids are dissolved in minimum DCM and loaded on a silica gel column 240, packed, for example, in 70:30 n-heptane:acetone. The column is eluted, and fractions containing pure product are concentrated 245. The purified product is dissolved in t-BME and added slowly to n-heptane 250. The precipitated solids are filtered, washed with n-heptane and dried 255. BHT is added to the solids, and the solids dissolved in acetone, filtered, and concentrated 260. The residue is treated with acetone twice 260 and concentrated each time to dryness. The product is then dried under vacuum 260.

In a third embodiment, sirolimus (rapamycin) is dissolved in dichloromethane. 2,6-Lutidine is added, and the solution is cooled to −30° C. Triflic anhydride is slowly added. After stirring the reaction, the solution is warmed to 10° C. The reaction solution is concentrated, and the residue dissolved in IPAC. 1-H-tetrazole, followed by DIEA are added, and the reaction mixture stirred at 22-25° C. The solution is then concentrated, and purified on a silica gel column eluting with, for example, 1:1 THF:heptane. The fractions containing the N-1 isomer are collected, pooled and concentrated. The resulting oil is dissolved in minimum DCM and loaded on a silica gel column packed in, for example, 65:35 heptane:acetone. The column is eluted with heptane:acetone, and the fractions containing the pure product are concentrated. The concentrate is dissolved in t-BME and added slowly to n-heptane with vigorous stirring. The precipitate is then stirred at 5-10° C. for not longer than 1 hour, filtered, washed with heptane and dried on the funnel with nitrogen. BHT is added to the solids, and the mixture dissolved in acetone. The solution is then passed through a filter and concentrated. The residue is treated with acetone two more times, and concentrated each time to dryness. The final product is dried under vacuum at 50° C.

Different reagents can be substituted in the methods of the invention to accomplish the invention. For example, 2,6-di-t-butyl pyridine and DIEA can replace 2,6-lutidine to make triflate. Other bases can be used at this step, including pyridine, other substituted pyridines, such as 2,6-di-tert-butylpyridine or 2,4,6-collidine, and 4-dimethylaminopyridine (DMAP), N-methylmorpholine and others that are apparent to one of skill in the art. Various solvents, bases (instead of DIEA) and nucleophiles (instead of tetrazole) can also be used in the methods of the invention. Examples are provided in Table 1 below.

TABLE 1

$S_N2$ Displacement reaction in various bases

| Reaction conditions | Comments |
|---|---|
| IPAc/DIEA | N-1 isomer favored |
| DCM/DIEA | Same ratio of isomers N-1:N-2 |
| IPAc/DIEA | ½ eq DIEA, slow reaction |
| DME/DIEA | Similar to IPAc |
| THF/DIEA | Similar to IPAc |
| Dioxane/DIEA | Same as IPAc |
| ACN/DIEA | Slow reaction, low ratio |
| DMA/DIEA | Decomposition |
| DMF/DIEA | Decomposition |
| IPAc/Lut | Very slow reaction, decomposition |
| IPAc/TEA | Slow, same ratio of isomers N-1:N-2 |
| IPAc/NMM | Slow reaction, N-2 isomer favored |
| THF/TEA | Low N-1:N-2 ratio |

TABLE 1-continued

S$_N$2 Displacement reaction in various bases

| Reaction conditions | Comments |
|---|---|
| IPAc/DBU | Heterogeneous reaction, N-2 isomer favored |
| IPAc/K$_2$CO$_3$ | Heterogeneous reaction, N-2 isomer favored |
| IPAC/DMAP | Heterogeneous reaction |
| IPAC/no base | Triflate decomposition |
| THF/KOtBu | Heterogeneous, slow, N-2 isomer favored, decomposition. |
| IPAc/DIEA | 33° C. heated, reaction rate increases |

Bases and solvents. Strong bases, such as 1,8-Diazabicyclo [5.4.0]undec-7-ene (DBU), potassium carbonate (K$_2$CO$_3$), 4-Dimethylaminopyridine (DMAP) and Potassium tert-butoxide (KOtBu) give extensive decomposition and generally favor N-2 isomer formation and are therefore not preferred. Weaker bases, such as lutidine, TEA and NMM slow the S$_N$2 reaction with formation of both N-1 and N-2 isomers in approximately 1:1 ratios. Aprotic solvents, such as IPAc, DME, dioxane, and THF perform well, favoring the N-1 isomer and are preferred. Using DCM gives isomers in approximately 1:1 ratio. Aprotic polar solvents like DMA and DMF lead to decomposition of the reaction product.

Temperature. The reaction can be accelerated by heating, although decomposition is usually observed. However, the reaction is usually completed by 4 hours or sooner; thus the reaction mixture can be processed earlier, minimizing degradation. Temperatures that are preferable to accelerate the SN2 displacement reaction include 20-35° C., preferably 22-33° C., more preferably 25-33° C., and most preferably 28-30° C.

Displacement nucleophiles. In general, 5-substituted tetrazoles can be substituted for tetrazole. For example, 5-methyl tetrazole and 5-phenyl tetrazole are preferred when substituting tetrazole. 5-substituted tetrazoles are preferred because they favor N-2 production of the N-2 isomer.

Anti-oxidants. To stabilize zotarolimus made by the one-pot processes, anti-oxidants can be used. They can be present in compositions to about 1% by weight, more preferably from 0.05% to 0.75%, and in the case of 3,5-di-tert-4-butylhydroxy toluene (BHT), 0.5%. Examples of anti-oxidants include 3,5-di-tert-4-butylhydroxy toluene, DL-α-tocopherol, propyl gallate, ascobyl palmitate, 3-tert-butyl-4-hydroxyanisole or 2-tert-butyl-4-hydroxyanisole, and fumaric acid. Preferably, the anti-oxidant is BHT.

EXAMPLES

Example 1

Dichloromethane-Toluene Isopropylacetate One-Pot Process with Filtration (1)

In this example, zotarolimus was prepared from rapamycin in a one-pot process using dichloromethane, toluene and isopropylacetate; the preparation was then purified, concentrated, and dried. The purified product was then characterized by its $^1$H, $^{13}$C NMR resonances from COSY, ROESY, TOCSY, HSQC, and HMBC spectra.

Rapamycin (10 g) was dissolved in dichloromethane (DCM, 25 ml) and toluene (50 ml). The reaction mixture was concentrated to dryness. This azeo-drying process was repeated twice with DCM/toluene. The foamy solid was dissolved in isopropylacetate (IPAc, 65 ml), and 2,6-Lutidine (3.2 ml) was added. The solution was cooled to −30° C. in acetonitrile-dry ice bath, and triflic anhydride (2.8 ml) was added slowly in 10 minutes. The reaction mixture was stirred for 30 minutes, and then filtered under nitrogen atmosphere. The salts were washed with IPAc (10 ml). 1-H-tetrazole (2.3 g), followed by diisopropylethylamine (DIEA, 7.4 ml) were added. The reaction mixture was stirred for 6 hours at room temperature, and then concentrated. The crude reaction mixture was purified on a silica gel column (350 g) eluting with 1:1 THF/heptane. The fractions containing product that eluted later (predominantly N-1 isomer) were collected and concentrated. The concentrated oil was dissolved in minimum DCM and loaded on a silica gel column packed in 65:35 heptane:acetone. The column was eluted with 65:35 heptane:acetone, and fractions containing pure product were concentrated.

The purified product was then dissolved in t-butylmethyl ether (t-BME, 13.5 g), and n-heptane (53 g) was added slowly with vigorous stirring. The precipitated solids were stirred at 5-10° C. for 2 hours, filtered, washed with heptane and dried on the funnel with nitrogen to give 3.2 g wet product. The solids (1.0 g) were dissolved in acetone (10 ml) and treated with 2,6-di-tert-butyl-4-ethylphenol (DEP, 0.2%). The solution was concentrated, dissolved in acetone (10 ml) and concentrated to dryness. The product was dried under vacuum for 18 hours at 47° C., yielding 0.83 g of zotarolimus. The product was characterized by its $^1$H, $^{13}$C NMR resonances from its COSY, ROESY, TOCSY, HSQC, and HMBC spectra.

$^1$H-NMR (DMSO-d6, position in bracket): ppm 0.73 (Me, 43); 0.81 (Me, 49); 0.84 (Me, 46); 0.89 (Me, 48); 0.98 (Me, 45); 1.41, 1.05 (CH2, 24); 1.18, 1.10 (CH2, 36); 1.52 (CH, 37); 1.53 (CH2, 12 & 42); 1.59, 1.30 (CH2, 5); 1.41, 1.67 (CH2, 4); 1.11, 1.73 (CH2, 38); 1.21, 1.83 (CH2, 15); 1.21, 1.83 (CH2, 13); 1.62 (Me, 44); 1.73 (Me, 47); 1.76 (CH, 35); 1.60, 2.09 (CH2, 3); 1.93, 2.21 (CH2, 41); 2.05 (CH, 11); 2.22 (CH, 23); 2.47 (CH, 25); 2.40, 2.77 (CH2, 33); 3.06 (OCH3, 50); 3.16 (OCH3, 51); 3.22, 3.44 (CH2, 6); 3.29 (OCH3, 52); 3.29 (CH, 31); 3.60 (CH, 39); 3.62 (CH, 16); 3.89 (CH, 27); 4.01 (CH, 14); 4.02 (CH, 28); 4.95 (CH, 2); 5.02 (CH, 34); 5.10 (=CH, 30); 5.17 (CH, 40); 5.24 (OH, 28); 5.46 (=CH, 22); 6.09 (=CH, 18); 6.15 (=CH, 21); 6.21 (=CH, 20); 6.42 (=CH, 19); 6.42 (OH, 10), 9.30 (CH, 53).

13C NMR (DMSO-d6, position in bracket): ppm 10.4 (Me, 44); 13.1 (Me, 47); 13.6 (Me, 46); 14.5 (Me, 49); 15.5 (Me, 43 & 48); 20.3 (CH2, 4); 21.6 (Me, 45); 24.4 (CH2, 4); 26.2 (CH2, 12); 26.4 (CH2, 3); 26.8 (CH2, 41); 27.2 (CH2, 42); 29.6 (CH2, 13); 31.6 (CH2, 38), 31.7 (CH, 37); 32.9 (CH, 35); 34.8 (CH, 11); 35.2 (CH, 23); 38.2 (CH2, 36); 39.1 (CH, 25); 39.4 (CH2, 33), 39.6 (CH2, 24), 40.0 (CH2, 15); 43.4 (CH2, 6); 45.2 (CH, 31); 50.6 (CH, 2); 55.4 (OCH3, 50); 55.8 (OCH3, 52); 57.0 (OCH3, 52); 55.9 (CH, 40); 66.2 (CH, 14); 73.4 (CH, 34); 75.6 (CH, 28); 77.4 (CH, 39); 82.3 (CH, 16); 85.7 (CH, 27); 99.0 (CH, 10); 125.3 (=CH, 30); 127.0 (=CH, 18 & 19); 130.4 (=CH, 21); 132.2 (=CH, 20); 137.2 (=CMe, 29); 137.7 (=CMe, 17); 139.2 (=CH, 22); 144.6 (CH, 53); 167.0 (C=O, 8); 169.1 (C=0, 1); 199.0 (C=O, 9); 207.5 (C=O, 32); 210.7 (C=O, 26).

Example 2

Dichloromethane-Isopropylacetate One-Pot Process (2)

In this example, zotarolimus was prepared from rapamycin in a one-pot process using dichloromethane and isopropylacetate. The compound was then purified, concentrated, and dried.

Rapamycin (10 g) was dissolved in dichloromethane (DCM, 100 g). 2,6-Lutidine (2.92 g) was added. The solution was cooled to −30° C. in acetonitrile-dry ice bath, and triflic anhydride (4.62 g) was added slowly in 10 minutes. The reaction mixture was stirred for 20 minutes, and then warmed to 10° C. within 15 minutes. The reaction solution was then concentrated. The residue was dissolved in IPAc (55 g). 1-H-tetrazole (2.68 g), followed by diisopropylethylamine (DIEA, 7.08 g) were then added. The reaction mixture was stirred for 6 hours at room temperature and then concentrated. The crude reaction mixture was purified on a silica gel column (360 g), eluting with 1:1 THF:heptane. The fractions containing product that eluted later (principally N-1) were collected and concentrated. The concentrated oil was dissolved in minimum DCM and loaded on a silica gel column (180 g) that was packed in 65:35 heptane:acetone. The column was then eluted with 65:35 heptane:acetone, and fractions containing pure product were concentrated.

The purified product was dissolved in t-butylmethyl ether (t-BME, 23 g) and added slowly to n-heptane (80 g) with vigorous stirring. The precipitated solids were stirred at 5-10° C. for not longer than 1 hour, filtered, washed with heptane and dried on the funnel with nitrogen. BHT (0.015 g) was added to the solids. The solids were dissolved in acetone (20 g), passed through a filter, and concentrated. The residue was treated with acetone two times (20 g), and concentrated each time to dryness. The product was then dried under vacuum for 18 h at not more than 50° C. to give 2.9 g of zotarolimus.

Example 3

Dichloromethane One-Pot Process (3)

In this example, zotarolimus was prepared from rapamycin in a one-pot process using dichloromethane. The compound was then purified, concentrated, and dried as described in Example 2.

Rapamycin (7.5 g) was dissolved in DCM (30 g). 2,6-Lutidine (1.76 g) was added. The solution was cooled to −30° C. in acetonitrile-dry ice bath, and triflic anhydride (2.89 g) was added slowly in 10 minutes. The reaction mixture was stirred for 20 minutes, and then assayed for the presence of rapamycin to determine consumption in the reaction. 1-H-tetrazole (1.44 g), followed by DIEA (5.29 g) was added. The reaction mixture was stirred for 6 hours at room temperature, and then directly loaded on a silica gel (270 g) column prepared in 1:1 THF:n-heptane (v/v). The crude reaction mixture was purified with 1:1 THF:n-heptane. The fractions containing product that elute later were collected and concentrated. The concentrated solids were dissolved in minimum DCM and loaded on a silica gel column (135 g) packed in 70:30 n-heptane:acetone. The column was eluted with 70:30 n-heptane:acetone, and fractions containing pure product, as identified by thin-layer chromatography (TLC), were concentrated.

The purified product was dissolved in t-BME (9 g), and added slowly to n-heptane (36 g) with vigorous stirring at 10±10° C. The precipitated solids were stirred at 5-10° C. for not longer than 1 hour, filtered, washed with n-heptane and dried on the funnel with nitrogen. BHT (0.006 g) was added to the solids. The solids were dissolved in acetone (20 g), passed through a filter, and concentrated. The residue was treated with acetone twice (20 g each) and concentrated each time to dryness. The product was dried under vacuum for not longer than 18 hours at not more than 50° C. to give 2.5 g of zotarolimus.

The above process, when carried out with rapamycin presence of 2,6-di-tert-butylpyridine or 2,4,6-collidine (2,3,5-trimethylpyridine) as a non-nucleophilic in step 1a gave zotarolimus of acceptable purity, but a lower yield.

Example 4

High-Pressure Liquid Chromatography (HPLC) purification of Zotarolimus Prepared by the One-Pot Synthesis Method In this example, zotarolimus was made from rapamycin using a one-pot synthesis method of the invention (using DCM), and then subjected to an additional round of purification using HPLC.

Rapamycin (3.75 g) was dissolved in dichloromethane (DCM, 15 g). 2,6-Lutidine (0.88 g) was then added. The solution was cooled to −30° C. in acetonitrile-dry ice bath, and triflic anhydride (1.45 g) was added slowly in 10 minutes. The reaction mixture was stirred for 20 minutes, and then 1-H-tetrazole (0.72 g), followed by DIEA (2.65 g) was added. The reaction mixture was stirred for 6 hours at 25° C., and then directly loaded on a silica gel (115 g) column prepared in 70:30 n-heptane:acetone. The crude reaction mixture was purified with 70:30 n-heptane:acetone. The fractions containing product were collected, and concentrated.

The concentrated solids were dissolved in acetonitrile-water and loaded on a C-18 TechniKrom column (5 cm×25 cm), and eluted with 64:36 acetonitrile-water containing 0.1% BHT. Fractions were analyzed by reverse phase (RP)-HPLC, and product fractions pooled and concentrated to remove acetonitrile. The product was extracted with ethyl acetate or isopropyl acetate, dried (sodium sulfate) and concentrated.

The purified product was dissolved in t-BME (4.5 g), and added slowly to n-heptane (18 g) with vigorous stirring at ~10° C. The precipitated solids were stirred at 5-10° C. for not longer than 1 hour, filtered, washed with n-heptane and dried on the funnel with nitrogen. BHT (0.005 g) was added to the solids. The solids were dissolved in acetone (20 g), passed through a filter, and concentrated. The residue was treated with acetone twice (20 g), and concentrated each time to dryness. The product was dried under vacuum for not longer than 18 hours at not more than 50° C. to give 1.2 g of high quality zotarolimus.

Example 5

Stability Analyses of Zotarolimus Prepared by One-Pot Synthesis Methods

This example demonstrates that zotarolimus prepared according to the methods of the invention can be stabilized using anti-oxidants.

Several lots of zotarolimus prepared by the one-pot methods lost significant potency over time. The potency loss was higher at increased temperature, but there was no apparent change in the impurity profile. Table 2 presents the potency of a lot of zotarolimus at various time intervals and temperature conditions. For example, even in a sealed container at room temperature (25° C.), potency decreases from 95.1% to 69.8% over 3 months. This loss was exacerbated in a sealed container when held at 40° C.—from 96.0% to 37.4% over just two months.

Subsequent investigation revealed that this loss of potency was due to oxidative degradation of the molecule that resulted in multiple degradation products. A stability study was carried out to prevent this oxidation using phenolic anti-oxidants and identified BHT as a suitable compound. Tables 3 and 4 present stability data using BHT at various concentrations (% represented w/w) and temperatures. For example, at 40° C., 0.5% BHT maintained potency from an initial 96.5% to a final potency of 95.9% over approximately three months, whereas under similar conditions in the absence of BHT, potency had nose-dived to 37.4% from 96% just after 2 months.

TABLE 2

Stability data of zotarolimus (temperature indicates storage; % potency)

| Time after synthesis | 5° C. (sealed) | 25° C. (sealed) | 25° C. (unsealed) | 40° C. (sealed) |
|---|---|---|---|---|
| Initial | 95.7 | 95.1 | 95.5 | 96.0 |
| 2 weeks | 98.2 | 95.7 | 98.0 | 81.1 |
| 1 month | 95.0 | 88.8 | 91.6 | 61.9 |
| 2 months | 95.4 | 81.6 | 87.1 | 37.4 |
| 3 months | 95.1 | 69.8 | 75.5 | Terminated |

TABLE 3

Zotarolimus stability with various concentrations of BHT at 4° C.

| BHT | 0.0% | 0.1% | 0.2% | 0.5% | 1.0% |
|---|---|---|---|---|---|
| 0 weeks | 97.2 | 96.7 | 96.3 | 96.5 | 95.9 |
| 2 weeks | 95.2 | 96.7 | 96.7 | 96.5 | 96.3 |
| 4 weeks | 96.4 | 97.3 | 97.5 | 96.2 | 96.6 |
| 6 weeks | 96.6 | 96.8 | 96.9 | 95.7 | 96.1 |
| 8 weeks | 97.5 | 96.9 | 96.9 | 96.9 | 96.9 |
| 12 weeks | 95.9 | 96.8 | 96.8 | — | 95.5 |

TABLE 4

Zotarolimus stability with various concentrations of BHT at 40° C.

| BHT (w/w) | 0.1% | 0.2% | 0.5% | 1.0% |
|---|---|---|---|---|
| 0 weeks | 96.7 | 96.3 | 96.5 | 95.9 |
| 2 weeks | 96.5 | 96.6 | 96.1 | 95.4 |
| 4 weeks | 96.9 | 97.2 | 96.4 | 96.4 |
| 6 weeks | 96.1 | 97.1 | 95.7 | 95.6 |
| 8 weeks | 96.2 | 97.0 | 96.1 | 96.5 |
| 12 weeks | 95.6 | — | 95.9 | 95.8 |

These stability studies confirm that in order to maintain purity, potency, and stability of zotarolimus, the addition of an antioxidant like BHT is very important.

Example 6

Isolation, and Characterization of Zotarolimus Equilibrium Isomers

Reverse-phase analysis of zotarolimus on a C-18 or phenyl column indicated that the major isomer, which eluted earlier, was the 6-member pyran form versus a 7-member oxepane (2) isomer, and the minor component oxepane isomer eluted 3-4 minutes later. On a normal phase HPLC (silica gel—YMC Co. Ltd; Kyoto, Japan), the two forms did not have a baseline separation; however oxepane form eluted just before the pyran form.

In order to demonstrate this equilibrium, each form was isolated by multiple HPLC injections of zotarolimus on a reverse phase phenyl column at pH 4. Each isolated form was then re-injected to study their equilibration at various intervals. The study indicated that the pyran form reached an equilibration state in 3-4 days, while the oxepane form (a minor component) had not completely equilibrated, even after almost 6 days. There was some formation of open ring acid during the study. The results of this study shown in Table 5 (with buffer) and in Table 6 (without buffer) clearly indicate that the two forms are under equilibrium, wherein the pyran form is more thermodynamically stable.

Studies were also carried out under non-buffered conditions in a solvent mixture of acetonitrile/water. Multiple injections of zotarolimus were performed on a C-18 Altima column (Alltech Associates, Inc.; Deerfield, Ill.) using 66% acetonitrile in water in a non-buffered media. The pyran and oxepane forms were collected. These forms were re-injected on C-18 column to study the equilibrium ratio at various intervals. These data, described in Tables 4 and 5, suggested that the equilibration between two isomers was rapid and completed within ~7-8 hours. These observations confirmed that zotarolimus exists in an equilibrium mixture of ~10:1 pyran (1) vs. oxepane (2) forms.

TABLE 5

Equilibration studies of pyran and oxepane forms of zotarolimus in pH 4 buffer

| Pyran (P) | | Oxepane (P-should this be "O"??) | |
|---|---|---|---|
| Time | Ratio P/O | Time | Ratio P/O |
| 1.5 hours | 99:1. | 0.5 hours | 1:99 |
| 3.5 hours | 98:2. | 3.5 hours | 18:82 |
| 5.5 hours | 97:3. | 5.5 hours | 27:71 |
| 7.5 hours | 96:4 | 7.5 hours | 36:63 |
| 50 hours | 92:8 | 50 hours | 70:28 |
| 5 days | 90:9 | 5 days | 83:16 |
| Ratio 6 days | 9.8:1 | Ratio 6 days | 6.6:1 |

TABLE 6

Equilibration studies of pyran and oxepane forms of zotarolimus without buffer

| Pyran (P) | | Oxepane (O) | |
|---|---|---|---|
| Time | Ratio P/O | Time | Ratio P/O |
| 2 hours | 90:9 | 1.5 hours | 26:70 |
| 3.5 hours | 88:9 | 3.5 hours | 80:17 |
| 5 hours | 87:9 | 5 hours | 87:10 |
| 8 hours | 86:9 | 7 hours | 88:9 |
| Ratio 8 hours | 9.8:1 | Ratio 7 hours | 10:1 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

Unless otherwise indicated, all references are herein incorporated by reference in their entireties.

REFERENCES

Baker, H., A. Sidorowicz, S. N. Sehgal, and C. Vezina. 1978. Rapamycin (AY-22,989), a new antifungal antibiotic. III. In vitro and in vivo evaluation. *J Antibiot (Tokyo)*. 31:539-45.

Caufield. U.S. Pat. No. 5,023,262. 1991. Hydrogenated Rapamycin Derivatives.

Caufield. WO 92/05179. 1992. Carboxylic Acid Esters of Rapamycin.

Eng. U.S. Pat. No. 4,401,653. 1983. Combination of Rapamycin and Picibanil for the Treatment of Tumors.

Failli. EPO 467606. 1992a. Rapamycin Derivatives.

Failli. U.S. Pat. No. 5,120,842. 1992b. Silyl Ethers of Rapamycin.

Failli. U.S. Pat. No. 5,177,203. 1993. Rapamycin 42-Sulfonates and 42-(N-Carboalkoxy) Sulfamates Useful as Immunosuppressive Agents.

Higuchi, T., and V. Stella. 1987. Pro-drugs as Novel Delivery systems.

Hughes, P., J. Musser, M. Conklin, and R. Russo. 1992. The isolation, synthesis and characterization of an isomeric form of rapamycin. *Tetrahedron Lttrs*. 33:4739-4742.

Kao. U.S. Pat. No. 5,120,725. 1992a. Bicyclic Rapamycins.

Kao. U.S. Pat. No. 5,120,727. 1992b. Rapamycin Dimers.

Martel, R. R., J. Klicius, and S. Galet. 1977. Inhibition of the immune response by rapamycin, a new antifungal antibiotic. *Can J Physiol Pharmacol*. 55:48-51.

Mollison, K. U.S. Pat. No. 6,015,815. 2000. Tetrazole-containing rapamycin analogs with shortened half-lives.

Mollison, K., A. LeCaptain, S. Burke, K. Cromack, P. Tarcha, Y.-C. J. Chen, and J. Toner. US Patent Application Publication 20030129215. 2003. Medical devices containing rapamycin analogs Paiva, N. L., A. L. Demain, and M. F. Roberts. 1991. Incorporation of acetate, propionate, and methionine into rapamycin by *Streptomyces hygroscopicus*. *J Nat Prod*. 54:167-77.

Roche, E. 1987. Bioreversible Carriers in Drug Design. American Pharmaceutical Association and Pergamon Press.

Sehgal, S. N. U.S. Pat. No. 3,929,992. 1975. Rapamycin and Process of Preparation.

Sehgal, S. N. U.S. Pat. No. 3,993,749. 1976. Rapamycin and Process of Preparation.

Sehgal, S. N., H. Baker, and C. Vezina. 1975. Rapamycin (AY-22,989), a new antifungal antibiotic. II. Fermentation, isolation and characterization. *J Antibiot (Tokyo)*. 28:727-32.

Surendra. U.S. Pat. No. 4,885,171. 1989. Use of Rapamycin in Treatment of Certain Tumors.

Vezina, C., A. Kudelski, and S. N. Sehgal. 1975. Rapamycin (AY-22,989), a new antifungal antibiotic. I. Taxonomy of the producing streptomycete and isolation of the active principle. *J Antibiot (Tokyo)*. 28:721-6.

We claim:

1. A method of preparing a molecule of formula I:

Formula I

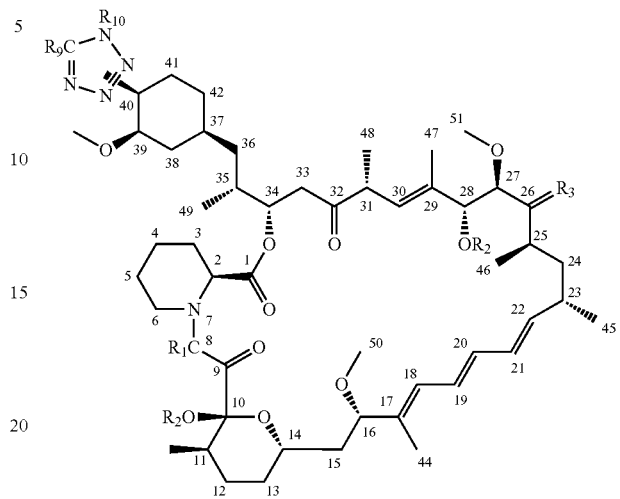

comprising:

(a) reacting a molecule of formula II:

Formula II

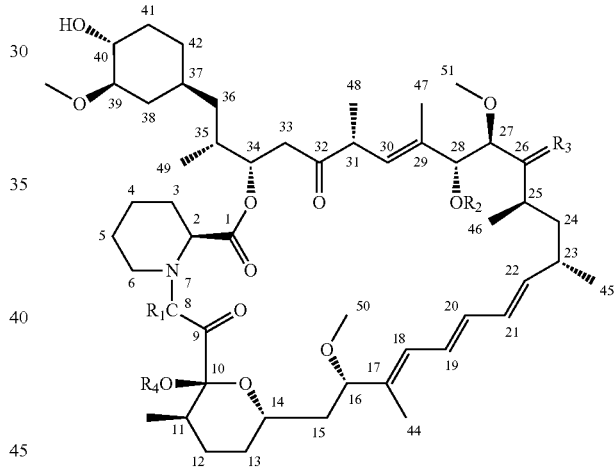

with triflic anhydride to produce a molecule of formula III:

Formula III

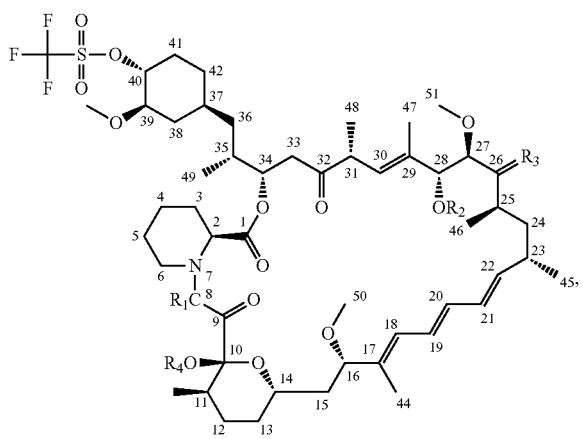

(b) reacting the molecule of formula III with a molecule of formula IV:

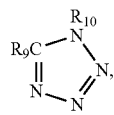

Formula IV and
(c) providing an antioxidant,
wherein
  $R_1$ is selected from the group consisting of =O, and (H, OH);
  $R_2$ and $R_5$ are independently selected from the group consisting of H, —C(=O)$R_6$, —C(=O)O$R_6$, —C(=O)NH$R_6$, and —C(=S)O$R_6$;
  $R_3$ is selected from the group consisting of =O and O$R_5$; or $R_2$ and $R_3$ can be taken together to form moiety of formula A—C($R_7$)($R_8$)—O—B, where A is a bond to oxygen bonded to carbon 28 and B is a bonded to carbon 28 as defined above;
  $R_4$ is selected from the group consisting of H and $C_1$-$C_4$ alkyl;
  $R_6$ is selected from the group consisting of $C_1$-$C_{10}$ alkyl, $C_3$-$C_6$ cycloalkyl, aryl groups, and heterocyclic groups;
  $R_7$ and $R_8$ are independently selected from the group consisting of H, $C_1$-$C_6$ alkyl, or $R_7$ and $R_8$ taken together are =O
  $R_9$ and $R_{10}$ are independently selected from the group consisting of H, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl,
  wherein the reactions are performed in a single pot,
  wherein the antioxidant is selected from the group consisting of 3,5-di-tert-4-butylhydroxy toluene (BHT), 2,6-di-t-butyl-4-ethylphenol (DEP), 2,6-di-t-butyl-4-methoxylphenol (DMP), DL-α-tocopherol, propyl gallate, ascobyl palmitate, 3-tert-butyl-4-hydroxyanisole, 2-tert-butyl-4-hydroxyanisole, fumaric acid, and combinations thereof.

2. The method of claim 1, wherein step (a) is carried out in the presence of a non-nucleophilic base.

3. The method of claim 2, wherein the non-nucleophilic base is selected from a substituted pyridine, diisopropylethyl amine and pyridine.

4. The method of claim 3, wherein the substituted pyridine is selected from 2,6-Lutidine, 2,6-di-tert-butylpyridine and 2,4,6-collidine.

5. The method of claim 2, wherein step (a) is carried out in the presence of a solvent.

6. The method of claim 5, wherein the solvent comprises isopropyl acetate or dichloromethane.

7. The method of claim 5, wherein the solvent comprises dichloromethane that is exchanged to isopropyl acetate before or during step (b).

8. The method of claim 1, wherein $R_{10}$ is H, and $R_9$ is one selected from the group consisting of H, methyl, and phenyl.

9. The method of claim 1, wherein $R_9$ and $R_{10}$ are H.

10. The method of claim 1, wherein step (b) is carried out in the presence of a solvent.

11. The method of claim 10, wherein the solvent is an aprotic solvent.

12. The method of claim 11, wherein the aprotic solvent is selected from the group consisting of perfluorohexane, α, α, α-trifluorotoluene, pentane, hexane, cyclohexane, methylcyclohexane, decahydronaphthalene, carbon tetrachloride, dioxane, fluorotrichloromethane, benzene, toluene, triethyl amine, carbon disulfide, diisopropyl ether, diethyl ether, t-butyl methyl ether, chloroform, ethyl acetate, 1,2-dimethoxyethane, 2-methoxyethyl ether, tetrahydrofuran, 1,2-dimethoxyethane, tetrahydrofuran, methylene chloride, pyridine, 2-butanone, acetone, hexamethylphosphoramide, N-methylpyrrolidinone, nitromethane, dimethyl formamide, acetonitrile, sulfolane, dimethyl sulfoxide, diisopropyl ethyl amine, isopropyl acetate, dichloromethane, N,N-dimethylformamide or propylene carbonate, and combinations thereof.

13. The method of claim 1, wherein step (b) is carried out in the presence of diisopropyl ethyl amine and a solvent selected from the group consisting of isopropyl acetate, dichloromethane, 1,2-dimethoxyethane, tetrahydrofuran and acetonitrile.

14. The method of claim 1, wherein step (b) is carried out in the presence of diisopropyl ethyl amine and either isopropyl acetate or dichloromethane.

15. The method of claim 1, wherein
  $R_1$ is =O
  $R_2$ is H
  $R_3$ is =O and
  $R_4$ is H.

16. A method of preparing a molecule of formula V:

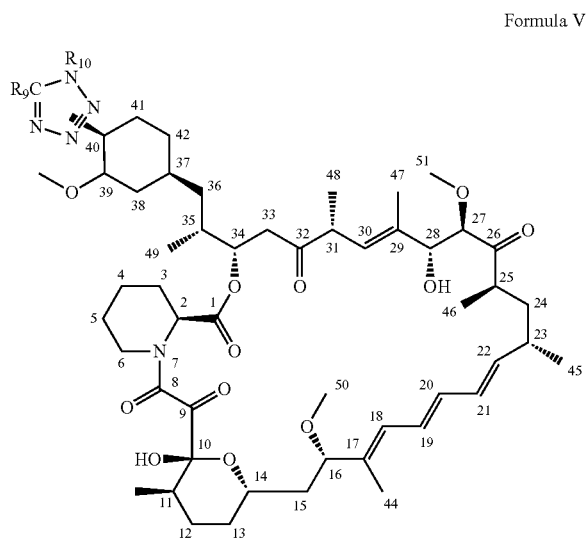

Formula V comprising:

(a) reacting a molecule of formula VI:

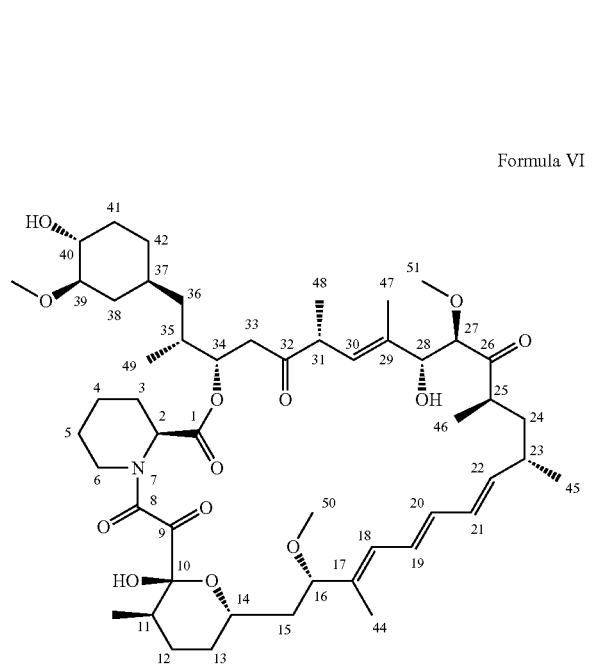

Formula VI with triflic anhydride to produce a molecule of formula VII:

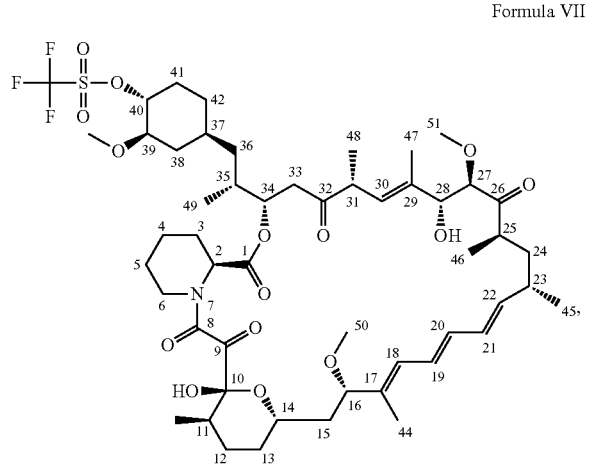

Formula VII (b) reacting the molecule of formula VII with a molecule of formula IV:

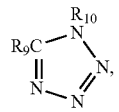

Formula IV and (c) providing an antioxidant, wherein $R_9$ and $R_{10}$ are independently selected from the group consisting of H, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl wherein the reactions are performed in a single pot, wherein the antioxidant is selected from the group consisting of 3,5-di-tert-4-butylhydroxy toluene (BHT), 2,6-di-t-butyl-4-ethylphenol (DEP), 2,6-di-t-butyl-4-methoxylphenol (DMP), DL-α-tocopherol, propyl gallate, ascobyl palmitate, 3-tert-butyl-4-hydroxyanisole, 2-tert-butyl-4-hydroxyanisole, fumaric acid, and combinations thereof.

17. The method of claim 16, wherein step (a) is carried out in the presence of a non-nucleophilic base.

18. The method of claim 17, wherein the non-nucleophilic base is selected from a substituted pyridine, diisopropylethyl amine and pyridine.

19. The method of claim 18, wherein the substituted pyridine is selected from 2,6-Lutidine, 2,6-di-tert-butylpyridine and 2,4,6-collidine.

20. The method of claim 18, wherein step (a) is carried out in the presence of a solvent.

21. The method of claim 20, wherein the solvent comprises isopropyl acetate or dichloromethane.

22. The method of claim 20, wherein the solvent comprises dichloromethane and is exchanged with isopropyl acetate before or during step (b).

23. The method of claim 16, wherein $R_{10}$ is H, and $R_9$ is selected from the group consisting of H, methyl, and phenyl.

24. The method of claim 16, wherein $R_9$ and $R_{10}$ are H.

25. The method of claim 16, wherein step (b) is carried out in the presence of a solvent.

26. The method of claim 25, wherein the solvent is an aprotic solvent.

27. The method of claim 26, wherein the aprotic solvent is selected from the group consisting of perfluorohexane, α,α,α-trifluorotoluene, pentane, hexane, cyclohexane, methylcyclohexane, decahydronaphthalene, carbon tetrachloride, dioxane, fluorotrichloromethane, benzene, toluene, triethyl amine, carbon disulfide, diisopropyl ether, diethyl ether, t-butyl methyl ether, chloroform, ethyl acetate, 1,2-dimethoxyethane, 2-methoxyethyl ether, tetrahydrofuran, 1,2-dimethoxyethane, tetrahydrofuran, methylene chloride, pyridine, 2-butanone, acetone, hexamethylphosphoramide, N-methylpyrrolidinone, nitromethane, dimethyl formamide, acetonitrile, sulfolane, dimethyl sulfoxide, diisopropyl ethyl amine, isopropyl acetate, dichloromethane, N,N-dimethylformamide or propylene carbonate, and combinations thereof.

28. The method of claim 16, wherein step (b) is carried out in the presence of diisopropyl ethyl amine and either isopropyl acetate or dichloromethane.

29. A composition comprising a molecule of formula I:

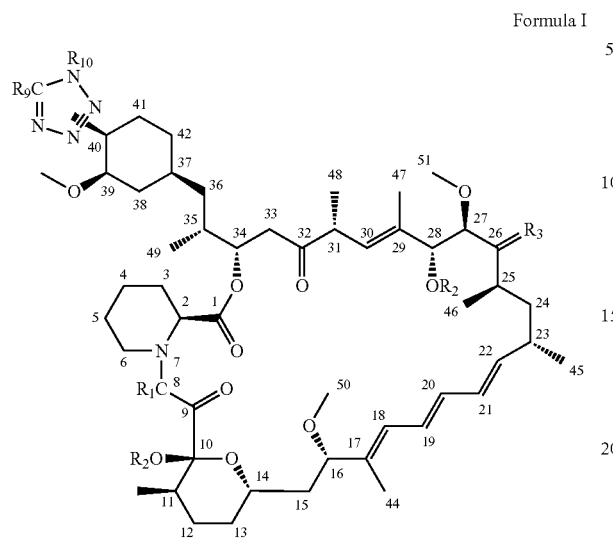

Formula I and an anti-oxidant,
  wherein
    $R_1$ is selected from the group consisting of =O and (H, OH);
    $R_2$ and $R_5$ are independently selected from the group consisting of H, —C(=O)$R_6$, —C(=O)O$R_6$, —C(=O)NH$R_6$, and —C(=S)O$R_6$;
    $R_3$ is selected from the group consisting of =O and O$R_5$; or $R_2$ and $R_3$ can be taken together to form moiety of formula A—C($R_7$)($R_8$)—O—B, where A is a bond to oxygen bonded to carbon 28 and B is a bonded to carbon 28 as defined above;
    $R_4$ is selected from the group consisting of H and $C_1$-$C_4$ alkyl;
    $R_6$ is selected from the group consisting of $C_1$-$C_{10}$ alkyl, $C_3$-$C_6$ cycloalkyl, aryl groups, and heterocyclic groups;
    $R_7$ and $R_8$ are independently selected from the group consisting of H, $C_1$-$C_6$ alkyl, or $R_7$ and $R_8$ taken together are =O,
    $R_9$ and $R_{10}$ are independently selected from the group consisting of H, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, and cycloalkenylalkyl, heterocyclyl,
  wherein the antioxidant is selected from the group consisting of 3,5-di-tert-4-butylhydroxy toluene (BHT), 2,6-di-t-butyl-4-ethylphenol (DEP), 2,6-di-t-butyl-4-methoxylphenol (DMP), DL-α-tocopherol, propyl gallate, ascobyl palmitate, 3-tert-butyl-4-hydroxyanisole, 2-tert-butyl-4-hydroxyanisole, fumaric acid, and combinations thereof.

30. The composition of claim 29, wherein the anti-oxidant comprises 3,5-di-tert-4-butylhydroxy toluene.

31. A composition comprising a molecule of formula V:

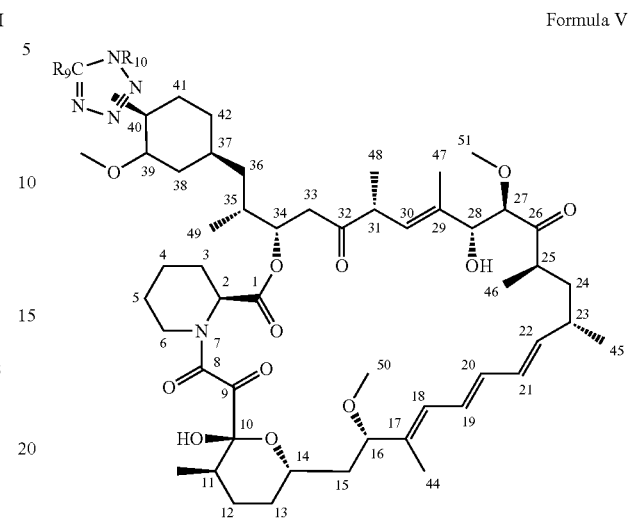

Formula V wherein
  $R_9$ and $R_{10}$ are independently selected from the group consisting of H, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl;
and an anti-oxidant,
  wherein the anti-oxidant is selected from the group consisting of 3,5-di-tert-4-butylhydroxy toluene (BHT), 2,6-di-t-butyl-4-ethylphenol (DEP), 2,6-di-t-butyl-4-methoxylphenol (DMP), DL-α-tocopherol, propyl gallate, ascobyl palmitate, 3-tert-butyl-4-hydroxyanisole, 2-tert-butyl-4-hydroxyanisole, fumaric acid, and combinations thereof.

32. The composition of claim 31, wherein the anti-oxidant comprises 3,5-di-tert-4-butylhydroxy toluene.

33. The composition of claim 32, wherein $R_9$ and $R_{10}$ are each a hydrogen.

34. The method of claim 1, further comprising a step of
  (d) purifying the reaction product using a silica gel column and using a mixture of THF and heptane as eluting solvent.

35. The method of claim 34, further comprising a step of
  (e) dissolving the product from step (d) in t-butylmethylether (t-BME) and then adding n-heptane to form a precipitate.

36. The method of claim 16, further comprising a step of
  (d) purifying the reaction product using a silica gel column and using a mixture of THF and heptane as eluting solvent.

37. The method of claim 36, further comprising a step of
  (e) dissolving the product from step (d) in t-butylmethylether (t-BME) and then adding n-heptane to form a precipitate.

* * * * *